US006673374B2

(12) United States Patent
Murad

(10) Patent No.: US 6,673,374 B2
(45) Date of Patent: Jan. 6, 2004

(54) PHARMACEUTICAL COMPOSITIONS AND METHODS FOR MANAGING SKIN CONDITIONS

(76) Inventor: Howard Murad, 4265 Marina City Dr., Marina del Rey, CA (US) 90292

( * ) Notice: Subject to any disclaimer, the term of this patent is extended or adjusted under 35 U.S.C. 154(b) by 0 days.

(21) Appl. No.: 09/953,431

(22) Filed: Sep. 17, 2001

(65) Prior Publication Data

US 2002/0054918 A1 May 9, 2002

Related U.S. Application Data

(63) Continuation-in-part of application No. 09/878,231, filed on Jun. 12, 2001, now Pat. No. 6,576,948, which is a continuation of application No. 09/549,202, filed on Apr. 13, 2000, now Pat. No. 6,296,880, which is a continuation-in-part of application No. 09/330,127, filed on Jun. 11, 1999, now Pat. No. 6,071,541.
(60) Provisional application No. 60/094,775, filed on Jul. 31, 1998.

(51) Int. Cl.[7] .................... A61K 33/40; A61K 31/415; A61K 31/045; A61K 31/19
(52) U.S. Cl. ................. 424/616; 514/248; 514/616; 514/714; 514/739
(58) Field of Search ................. 514/714, 739, 514/460, 248; 424/616

(56) References Cited

U.S. PATENT DOCUMENTS

| | | | |
|---|---|---|---|
| 3,297,456 A | 1/1967 | Newell | 106/3 |
| 4,051,058 A | 9/1977 | Bowing et al. | 252/186 |
| 4,051,059 A | 9/1977 | Bowing et al. | 252/186 |
| 4,178,372 A * | 12/1979 | Coats | 424/744 |
| 4,203,765 A | 5/1980 | Claeys et al. | 430/252 |
| 4,438,102 A | 3/1984 | Ganci | 424/130 |
| 4,514,384 A * | 4/1985 | Gallina | 514/179 |
| 4,534,945 A | 8/1985 | Hopkins et al. | 423/273 |
| 4,557,898 A * | 12/1985 | Greene et al. | 422/28 |
| 4,557,935 A | 12/1985 | af Ekenstam et al. | 424/130 |
| 4,900,721 A | 2/1990 | Bansemir et al. | 514/25 |
| 5,008,030 A | 4/1991 | Cook et al. | 510/384 |
| 5,139,788 A | 8/1992 | Schmidt | 424/616 |
| 5,177,099 A | 1/1993 | Rovati et al. | |
| 5,296,215 A | 3/1994 | Burke et al. | 424/49 |
| 5,357,636 A | 10/1994 | Dresdner, Jr. et al. | 2/161.7 |
| 5,474,768 A * | 12/1995 | Robinson | 424/78.31 |
| 5,519,059 A | 5/1996 | Sawaya | |
| 5,547,990 A | 8/1996 | Hall et al. | 514/563 |
| 5,593,952 A | 1/1997 | Jarrett | 507/131 |
| 5,641,475 A | 6/1997 | Yu et al. | 424/65 |
| 5,693,318 A | 12/1997 | Burke et al. | 424/78.02 |
| 5,695,745 A | 12/1997 | Barton et al. | 424/49 |
| 5,843,998 A * | 12/1998 | Song et al. | 514/588 |
| 5,861,432 A | 1/1999 | Skiar | |
| 5,869,062 A | 2/1999 | Oliver | 424/195.1 |
| 5,951,993 A | 9/1999 | Scholz et al. | 424/405 |
| 5,958,984 A | 9/1999 | Devillez | 514/714 |
| 6,022,547 A * | 2/2000 | Herb et al. | 424/401 |
| 6,491,928 B1 * | 12/2002 | Smith, III | 424/401 |
| 6,495,150 B2 * | 12/2002 | Bekele | 424/401 |

FOREIGN PATENT DOCUMENTS

| | | |
|---|---|---|
| CA | 1 174 976 | 9/1984 |
| EP | 0 191 214 A2 | 8/1986 |
| EP | 2 250 539 B1 | 5/1991 |
| EP | 0 425 507 B1 | 2/1995 |
| GB | 1135643 | 12/1968 |
| GB | 2 076 286 A | 12/1981 |
| GB | 2 189 394 B | 10/1987 |

OTHER PUBLICATIONS

Wile et al., Hexetidine ('Oraldene'): a report on . . . , abstract, Current. Med. res. Opin., 1986, vol. 10(2), pp. 82–88.
De grandis et al., Undecylenic acid derivatives for the treatment of mycosis . . . , abstract, Rib. ital. Essenze, profumi, . . . 1974, vol. 56(7), pp. 371–379.
Mills et al., Therapeutic Options in the Management of Acne and its Variants, Seminars in Dermatology, 1982, vol. I(4), pp. 233–237.

* cited by examiner

Primary Examiner—Vickie Kim
(74) Attorney, Agent, or Firm—Pennie & Edmonds LLP

(57) ABSTRACT

This application relates to a pharmaceutical composition and methods for treating inflammatory skin conditions. The compositions include hydrogen peroxide, one or more moisturizing agents, and an anti-inflammatory agent. The pharmaceutical compositions may optionally include one or more exfoliants. The compositions can be used to treat inflammatory skin conditions such as dermatitis, including, but not limited to seborrheic dermatitis, nummular dermatitis, contact dermatitis, atopic dermatitis, exfoliative dermatitis, perioral dermatitis, and stasis dermatitis; psoriasis; folliculitis; rosacea; acne; impetigo; erysipelas; paronychia, erythrasma; and eczema.

12 Claims, No Drawings

PHARMACEUTICAL COMPOSITIONS AND METHODS FOR MANAGING SKIN CONDITIONS

CROSS-REFERENCE TO RELATED APPLICATIONS

This application is a continuation-in-part of application Ser. No. 09/878,231, filed Jun. 12, 2001, currently U.S. Pat. No. 6,576,948, of which is a continuation of application Ser. No. 09/549,202, filed Apr. 13, 2000, now U.S. Pat. No. 6,296,880, which is a continuation-in-part of application Ser. No. 09/330,127, filed Jun. 11, 1999, currently U.S. Pat. No. 6,071,541, which is a continuation-in-part of provisional application Ser. No. 60/094,775, filed Jul. 31, 1998.

TECHNICAL FIELD

This application relates to pharmaceutical compositions and methods to cleanse skin and facilitate the prevention, treatment, and management of skin conditions.

BACKGROUND OF THE INVENTION

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by, for example, dryness, yeast, and structural changes in the skin, such as due to aging and excessive sun exposure.

Various pharmaceuticals have been used for the treatment or prevention of skin conditions, including skin cleansing compositions. Some of these compositions are discussed below.

Canadian Patent No. 1,174,976 discloses a germ-killing skin medication including two gels to be applied and mixed in situ, the first gel having sodium chlorite in an aqueous form and the second gel having lactic acid in an aqueous gel.

Great Britain Application No. 2,076,286 A discloses a dermatological composition of an oil medium dispersed in an aqueous medium that contains hydrogen peroxide, a buffer to maintain the composition below a pH of 7, and a starch gelled in situ. The buffer may include lactic, citric, tartaric, maleic, or hydroxysuccinic acids with an acid salt.

Great Britain Application No. 2,189,394 A discloses a concentrate that can be mixed with hydrogen peroxide to become an effective disinfectant for water, foodstuff, animal feeds, equipment, packages, and the like. The concentrate includes an inorganic acid with a pH less than 1.6, a silver compound or colloidal silver, an organic acid stabilizer such as tartaric, lactic, salicylic, or citric acid, and optionally gelatin. European Patent Application No. 0,191,214 A2 discloses a cosmetic liquid cleanser for treating blemished, scarred, or inflamed skin having boric acid or borax, ammonium hydroxide, a peroxide, and optionally salicylic acid.

European Patent No. 0,250,539 B1 discloses a stabilized aqueous hydrogen peroxide composition having 0.1 to 4 weight percent hydrogen peroxide and 0.5 to 5 weight 2 percent 13-crystals of one or more lipids selected from monoglycerides of fatty acids, ascorbic acid, phosphate or lactic acid esters of fatty acids and monoglycerol ethers, said fatty acids and ether chains being saturated and having 12 to 18 carbons.

European Patent No. 0,425,507 B1 discloses compositions for treating abnormal or damaged conditions of the epithelium including skin, which include 0.01 to 12 weight percent of an activated protein containing at least 0.5 weight percent cysteine, 0.1 to 15 weight percent of a reducing agent to reduce cystine to cysteine, and 81.0 to 99.889 weight percent water, acids, bases, buffering agents, emulsifying agents, thickeners, solvents, preservatives, coloring agents, and perfuming agents. The reducing agent may be a salt of a thioglycolic acid. In a preferred embodiment, the composition also includes an oxidizing agent, such as hydrogen peroxide.

U.S. Pat. No. 3,297,456 discloses cleaning and polishing compositions, particularly for floor waxing, having lactic acid, methanol, hydrogen peroxide, and aqua ammonia in a particular ratio.

U.S. Pat. Nos. 4,051,058 and 4,051,059 disclose stable peroxy-containing concentrates useful for the production of microbicidal agents consisting essentially of an aqueous mixture of 0.5 to 20 weight percent peracetic or perpropionic acid or their precursors, 25 to 40 weight percent hydrogen peroxide, and optionally up to 5 weight percent anionic surface-active compounds of the sulfonate and sulfate type. Also disclosed are compositions that further include 0.25 to 10 weight percent organic phosphonic acid capable of sequestering bivalent metal cations and their water-soluble acid salts.

U.S. Pat. No. 4,203,765 discloses an aqueous acidic etch-bleach solution of hydrogen peroxide, iron ions, and inorganic anions that form a silver salt, such that in the dissolved state the solution contains citric acid and a polymer of alkylene oxide units for stabilization of the hydrogen peroxide.

U.S. Pat. No. 4,438,102 discloses compositions containing gelatin, hydrogen peroxide, ammonium hydroxide, thioglycolic acid, and a lower alkanol to promote the growth of dermal and epidermal tissue.

U.S. Pat. No. 4,534,945 discloses an aqueous 25 to 35 weight percent 2 solution of hydrogen peroxide stabilized against decomposition with up to 1.4 mg/L tin, which is maintained in solution by particular amounts of phosphate in the form of phosphonic acid and hydroxycarboxylic acid.

U.S. Pat. No. 4,557,935 discloses a germicidal composition of hydrophilic lipid crystals of 1-monolaurin, and preferably 1-monomyristin, and hydrogen peroxide, whereby the former stabilize the latter. Optionally, the compositions further contain salicylic acid.

U.S. Pat. No. 4,900,721 discloses liquid, aqueous disinfectants based on alcohol and hydrogen peroxide that contain one or more $C_{2-8}$ alcohols, hydrogen peroxide or a hydrogen peroxide forming compound, one or more carboxylic acids, one or more microbicidally active nitrogen-containing organic compounds, one or more microbicidally active phenolic compounds for disinfection of the skin and mucous membrane.

U.S. Pat. No. 5,139,788 discloses an antimicrobial surface sanitizing composition having a diluent and antimicrobial agent of an antimicrobially effective amount of alphahydroxyacid substituted mono- or di-carboxylic acid and an antimicrobially effective amount of hydrogen peroxide, such that the composition leaves a non-contaminating residue after contact with surfaces to be disinfected.

U.S. Pat. No. 5,693,318 discloses phosphate esters for the improvement of water solubility of salicylic acid and peroxide compounds in an aqueous cleanser.

Despite these references, there remains a need for improved pharmaceutical compositions and methods of treating inflammatory skin conditions.

SUMMARY OF THE INVENTION

The present invention relates to a topical anti-inflammatory pharmaceutical composition that includes hydrogen peroxide in an amount sufficient to cleanse the skin; a moisturizing agent in an amount sufficient to facilitates hydration of the skin; and an anti-inflammatory agent to in an amount sufficient to reduce inflammation of the skin. The hydrogen peroxide is present in an amount from about 0.01 to 6 weight percent by weight of the composition, the moisturizing agent is present in an amount of about 0.01 to 20 weight percent by weight of the composition, and the anti-inflammatory agent is present in an amount of about 0.02 to 2 weight percent by weight of the composition.

The moisturizing agent can be a hydrophobic moisturizing agent such as ceramide, borage oil, tocopherol, tocopherol linoleate, dimethicone, glycerine, or a mixture thereof or a hydrophilic moisturizing agent such as hyaluronic acid, sodium peroxylinecarbolic acid, wheat protein, hair keratin amino acids, or a mixture thereof. The pharmaceutical composition can further include a pharmaceutically acceptable carrier or excipient. The pharmaceutical composition can be a gel, paste, cream, lotion, emulsion, or ointment.

The pharmaceutical composition may further include an exfoliant. The exfoliant can be an enzymatic exfoliant or a mono- or -poly-hydroxy acid such as alpha-hydroxy acid, beta-hydroxy acid, or tannic acid. In one embodiment the exfoliant is glycolic acid, lactic acid, citric acid, salicylic acid, or tannic acid.

The pharmaceutical composition may also include an amount of amphoteric surfactant and an amount of citric acid sufficient to inhibit hydrogen peroxide decomposition for at least three months, preferably for 3 months at 40° C. The pharmaceutical composition may also include at least one of a surfactant, a stabilizer, a preservative, an antioxidant, or a coloring agent, which together may be present in an amount from about 10.1 to 99.1 weight percent of the composition.

The invention also relates to a method of managing an inflammatory skin condition which comprises topically administering to a patient a therapeutically effective amount of hydrogen peroxide in an amount sufficient to cleanse the skin; a moisturizing agent in an amount sufficient to facilitates hydration of the skin; and an anti-inflammatory agent to in an amount sufficient to reduce inflammation of the skin. The skin condition can be dermatitis, psoriasis, folliculitis, rosacea, acne, impetigo, erysipelas, paronychia, erythrasma, and eczema. The amount of the hydrogen peroxide, moisturizing agent, and anti-inflammatory agent administered is about 1 mg to 20,000 mg per day.

The method can further involve administering one or more second dermatological agents selected from a moisturizer, anti-inflammatory agent, analgesic, or anesthetic by a route other than topical administration. The one or more second dermatological agents can be a moisturizer selected from panthenol, primrose oil, omega-3 fish oils, omega-6 fish oils, linoleic acid, flax seed oil, and mixtures thereof. The one or more second dermatological agents can be an anti-inflammatory agent selected from aspirin, ibuprofen, ketoprofen, naproxen, and mixtures thereof.

The method can also include administering one or more exfoliants in an amount sufficient to exfoliate at least a portion of the skin. The exfoliant can be an enzymatic exfoliant or a mono- or -poly-hydroxy acid. In one embodiment the exfoliant an alpha-hydroxy acid, beta-hydroxy acid, or tannic acid. In another embodiment the exfoliant is glycolic acid, lactic acid, citric acid, salicylic acid, or tannic acid.

DETAILED DESCRIPTION OF THE PREFERRED EMBODIMENTS

The present invention is directed to a pharmaceutical composition for the prevention, treatment, and management of inflammatory skin conditions. The management of inflammatory skin conditions can advantageously be accomplished by the administration of the pharmaceutical compositions of the present invention. Accordingly, methods for administering the compositions for management of an inflammatory skin condition are also encompassed by the invention. The methods are used for the prevention, treatment, or management of one or more inflammatory skin conditions.

The term "inflammatory skin conditions," as used herein, means conditions present any where on the skin that causes inflammation, i.e., reddening, pain, or swelling of the skin and which may be accompanied by a rash, sores, blisters or other skin eruptions. Examples of inflammatory skin conditions include, but are not limited to, dermatitis, including, but not limited to seborrheic dermatitis, nummular dermatitis, contact dermatitis, atopic dermatitis, exfoliative dermatitis, perioral dermatitis, and stasis dermatitis; psoriasis; folliculitis; rosacea; acne; impetigo; erysipelas; paronychia, erythrasma; eczema; and the like.

The terms "managing" or "management," as used herein, includes one or more of the prevention, treatment, or modification of a skin condition.

The hydrogen peroxide is present in an amount sufficient to cleanse at least a portion of the skin. "Cleanse" as used herein includes the removal of dirt, debris, air pollutants, desquamating cells, and cutaneous secretions of the skin. Preferably, the hydrogen peroxide is present in an amount to cleanse the skin without substantial irritation. The hydrogen peroxide is typically present in an amount from about 0.01 to 6 weight percent, preferably 0.05 to 4 weight percent, and more preferably 0.1 to 1 weight percent of the composition. Without wishing to be bound by theory it is believed that cleansing the skin with hydrogen peroxide improves penetration of the anti-inflammatory into the skin.

The pharmaceutical compositions include one or more moisturizing agents. "Moisturizing agent," as used herein, is used to include any agent that facilitates hydration of the skin by inhibiting or preventing loss of water from the skin, absorbs water from the atmosphere and hydrates the skin, or enhances the skin's own ability to absorb water directly from the atmosphere, or a combination thereof. Without wishing to be bound by theory it is believed that the moisturizing agent also improves the skins ability to absorb the anti-inflammatory agent. Furthermore, moisturizing agents also minimize or prevent the skin from drying and cracking; cracked skin is more susceptible to environmental factors that generate free radicals, which are believed to cause further damage to the skin. Suitable moisturizing agents include, but are not limited to, hydrophobic agents, and hydrophilic agents, or combinations thereof. Moisturizers, when used, are typically present in an amount from about 0.01 to 20 weight percent, preferably about 0.05 to 10 weight percent, more preferably from about 0.1 to 5 weight percent of the composition. Moisturizing agents that are hydrophobic agents include, but are not limited to, ceramide, borage oil (linoleic acid), tocopherol (Vitamin E), tocopherol linoleate, dimethicone, glycerine, and mixtures thereof. Hydrophobic agents, when present, are believed to moisturize the skin by inhibiting or preventing the loss of water from the skin. The hydrophobic agent, when present, is typically present in an amount from about 0.01 to 20 weight percent, preferably from about 0.05 to 15 weight percent, and more preferably from about 0.1 to 5 weight percent of the composition.

Moisturizing agents that are hydrophilic agents include, but are not limited to, hyaluronic acid, sodium peroxylinecarbolic acid (sodium PCA), wheat protein (e.g., laurdimonium hydroxypropyl hydrolyzed wheat protein), hair keratin amino acids, and mixtures thereof. Sodium chloride may also be present, particularly when hair keratin amino acids are included as a moisturizer. Hydrophilic agents, when present, are believed to moisturize the skin by absorbing moisture from the atmosphere to hydrate or facilitate hydration of the skin. The hydrophilic agent, when present, is typically present in an amount from about 0.01 to 20 weight percent, preferably from about 0.05 to 15 weight percent, and more preferably from about 0.1 to 5 weight percent of the composition.

Other moisturizing agents that hydrate the skin and are useful in the compositions and methods of the present invention include, but are not limited to, panthenol; primrose oil; GLA 3 and other fish oils that may include, for example, the omega-3 and omega-6 oils and/or linoleic acid; and flax seed oil. Preferably, these moisturizing agents are administered orally.

The compositions and methods for managing inflammatory skin conditions also include one or more anti-inflammatory agents in an amount sufficient to reduce inflammation of the skin. In one embodiment the anti-inflammatory agent is a steroidal anti-inflammatory. Suitable steroidal anti-inflammatory agents for use in the compositions and methods of the invention include the corticosteroids such as, but not limited to, hydrocortisone, fluocinolone acetonide, halcinonide, halobetasol propionate, clobetasol propionate, betamethasone dipropionate, betamethasone valerate, and triamcinolone acetonide.

In another embodiment the anti-inflammatory agent is a non-steroidal anti-inflammatory agent. Examples of suitable non-steroidal anti-inflammatory agents for use in the compositions and methods of the invention include, but are not limited to, aspirin, ibuprofen, ketoprofen, and naproxen. These anti-inflammatory agents are preferably administered orally. Other non-steroidal anti-inflammatory agents useful in the compositions of the invention include, but are not limited to aloe vera gel, aloe vera, licorice extract, pilewort, Canadian willow root, and zinc, and allantoin. Allantoin is a preferred non-steroidal anti-inflammatory agent. The anti-inflammatory agents are used in an amount sufficient to inhibit or reduce inflammation, preferably in an amount from about 0.02 to 2 weight percent, preferably from about 0.1 to 1.5 weight percent, and more preferably from about 0.2 to 1 weight percent of the composition. It should be understood, with reference to managing skin conditions, that the anti-inflammatory agents facilitate inhibition or suppression of inflammation anywhere on the skin. *Arnica Montana* (a healing herb) and vitamin K can also be used as the anti-inflammatory. *Arnica Montana* facilitates skin healing and acts as an antiseptic and local anti-inflammatory, and, when used, is typically present in an amount from about 0.1 to 2 weight percent, preferably about 0.2 to 1 weight percent. The Vitamin K inhibits 2 or suppresses inflammation and bruising (i.e., acts as an anti-inflammatory and anti-bruising agent) and, when used, is typically present in an amount from about 0.01 to 1 weight percent, preferably from about 0.1 to 0.5 weight percent.

Without wishing to be bound by theory it is believed that the components of the invention interact in a synergistic manner to provide the desired management of the skin. Together, the hydrogen peroxide, moisturizing agent, and anti-inflammatory agent cleanse the skin, remove substances foreign to the skin, and moisturize the skin to improve penetration of the anti-inflammatory agent to inhibit or reduce inflammation of the skin and generally facilitate management of inflammatory skin conditions. In particular, the compositions of the invention reduce or eliminate the redness, swelling, sores, and blisters typically associated with inflammatory skin conditions. The synergistic effect provides a composition for treating inflammatory skin conditions that is superior to using the anti-inflammatory alone.

In a preferred embodiment, the dermatological agent further includes an exfoliant to help remove dead or dying skin cells and further improve the skin's own ability to absorb moisture directly from the atmosphere in combination with one or more hydrophilic agents to help absorb moisture from the atmosphere and hydrate the skin or in combination with one or more a hydrophobic agents to inhibit or prevent moisture loss by the skin. More preferably, the pharmaceutical composition includes one or more of a hydrophilic agent and one or more of a hydrophobic agent in combination with an exfoliant. It is also believed that the exfoliant also helps the anti-inflammatory component penetrate the skin.

The exfoliant may be an enzymatic exfoliant, or an acidic exfoliant. Any enzymatic exfoliant known to those skilled in the art may be used in the compositions and methods of the invention. Examples of enzymatic exfoliants useful in the compositions and methods of the invention include, but are not limited to, papain, from papaya, and bromalein, from pineapple.

Examples of acidic exfoliants include, but are not limited to a mono- or poly-hydroxy acid, tannic acid, or a mixture thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. One of ordinary skill in the art would typically select one or more of the following mono- or poly-hydroxy acids: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid;

5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof; and 2-hydroxyphenyl pyruvic acid and esters thereof.

In one embodiment the poly-hydroxy acidic components is an alpha-hydroxy acid. Preferred alpha-hydroxy acids include citric acid, glycolic acid, lactic acid. In another embodiment the poly-hydroxy acidic exfoliant is a beta-hydroxy acid. A preferred beta-hydroxy acid is salicylic acid.

The term "pharmaceutically acceptable salt" refers to a salt prepared from pharmaceutically acceptable non-toxic acid. Examples of suitable inorganic metallic bases for salts formation with the acid compounds of the invention include, but are not limited to, aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370 are also suitable for use in the compositions and methods of the invention. The acidic component is present in the composition and methods in an amount sufficient to exfoliate, i.e., remove dead or dying skin cells, from at least a portion of the skin. The acidic component is typically present in an amount from about 0.1 to 12 weight percent, preferably about 1 to 11 weight percent, more preferably from about 4 to 10 weight percent of the composition. For example, the acidic component may be from about 0.1 to 3 weight percent citric acid in combination with up to about 2 weight percent salicylic acid.

In another embodiment, the pharmaceutical compositions further comprise a pharmaceutically acceptable antimicrobial agent. Any pharmaceutically acceptable antimicrobial agent available to those of ordinary skill in the art may be used, but preferably at least one of an antibacterial agent, antifungal agent, antiviral agent, or anthelmintic will be used according to the invention. A single broad spectrum antimicrobial agent, i.e., one that is believed to have at least two of antibacterial, antifungal, and antiviral efficacy, include: echinacea, golden seal, benzalkonium chloride, benzethonium chloride, iodine, grape seed extract, pomegranate extract, green tea extract or polyphenols, and the like, or combinations thereof, may be included. Another suitable antimicrobial agent includes the class of anthelmintics, such as metronidazole, to facilitate treatment of, e.g., tricomona infection. Preferred antiviral agents include, but are not limited to, acyclovir, tamvir, penciclovir, and the like, and mixtures thereof. Preferred antibacterial agents include, but are not limited to, triclosan, neomycin, polymyxin, bacitracin, clindamycin, benzoyl peroxide, a tetracycline, a sulfa drug, a penicillin, a quinolone, a cephalosporin, and mixtures thereof. Preferred antifungal agents include, but are not limited to, famesol, econazole, fluconazole, clotrimazole, ketoconazole, calcium or zinc undecylenate, undecylenic acid, butenafine hydrochloride, ciclopirox olaimine, miconazole nitrate, nystatin, sulconazole, terbinafine hydrochloride, and the like, and mixtures thereof. Exemplary tetracyclines include doxycycline and minocycline. An exemplary sulfa drug includes sulfacetamde. An exemplary cephalosporin includes cephalexin (commercially available as KEFLEX). Exemplary quinolones include the floxacins, such as loemfloxacin, of loxacin, and trovafloxacin. It should be readily understood that any salts, isomers, pro-drugs, metabolites, or other derivatives of these antimicrobial agents may also be included as the antimicrobial agent in accordance with the invention. The antimicrobial agent is typically present in an amount from about 0.01 to 1.5 weight percent, preferably from about 0.1 to 1.2 weight percent, and more preferably from about 0.3 to 1 weight percent of the composition. The antimicrobial agent inhibits the formation, and may further reduce, the presence of microbes that cause redness, inflammation, and irritation of the skin.

In another embodiment, the compositions further include one or more of a vitamin A source including retinyl palmitate or other retinyl esters, retinoic acid, or Retinol. The Retinol facilitates normal skin production, particularly epidermal normalization, and, when used, is typically present in an amount from about 0.01 to 6 weight percent, preferably about 0.1 to 5 weight percent.

The compositions of the invention may further include one or more surfactants, stabilizers, preservatives, coloring agents, anti-oxidants, water, buffering agents, emulsifying agents, thickeners, solvents, perfuming agents, and the like. Preferably, the water is deionized water. It should be understood that water includes the remainder of a given composition after other ingredients are determined. Although any pharmaceutically acceptable surfactant, stabilizer, preservative, coloring agent, buffering agents, emulsifying agents, thickeners, solvents, or perfuming agents may be used, certain compounds or mixtures are preferred as discussed below.

Preferred surfactants, including both the foaming and non-foaming type, including, but not limited to, sodium laureth sulfate, sodium laureth-13 carboxylate, disodium laureth sulfosuccinate, disodium cocoamphodiacetate, and the like, andmixtures thereof. More preferably, at least one amphoteric surfactant is included in the composition, such as disodium cocoamphodiacetate. The amphoteric surfactant, in combination with citric acid, inhibits hydrogen peroxide decomposition. The surfactant component may be present in an amount from about 10 to 90 weight percent, preferably about 20 to 80, and more preferably about 30 to 70 weight percent of the composition.

The term "inhibit hydrogen peroxide decomposition," as used herein, means to at least stop the rate of decomposition from increasing, preferably to inhibit the decomposition entirely, and more preferably to substantially inhibit the decomposition altogether. "Substantially inhibit," as used herein, means that less than about 10 weight percent, preferably less than about 3 weight percent, and more preferably less than about 1 weight percent, of the hydrogen peroxide decomposes over a three month period of time.

A preferred stabilizer includes glycol stearate or PEG-150 distearate. The stabilizer, when used, is typically present in an amount from about 0.1 to 5 weight percent of the composition.

Preferred preservatives include tetrasodium ethylenediamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 weight percent, preferably about 0.05 to 4 weight percent, and more preferably from about 0.1 to 2 weight percent.

Preferred coloring agents include FD&C Green No. 3, Ext. D&C Violet No. 2, FD&C Yellow No. 5, FD&C Red No. 40, and the like, and mixtures thereof. The coloring agents, when used, are typically present in an amount from about 0.001 to 0.1 weight percent, and preferably from about 0.005 to 0.05 weight percent of the composition.

Anti-oxidants of both the enzymatic and non-enzymatic type may be included in the compositions and methods of the invention. For example, superoxide dismutase (SOD), catalase, and glutathione peroxidase are natural enzymatic anti-oxidants used by the body that may be supplemented with the compositions herein. Suitable non-enzymatic anti-oxidants include, but are not limited to, Vitamin E (e.g., tocopherol), Vitamin C (ascorbic acid), carotenoids, Echinacoside and caffeoyl derivatives, oligomeric proanthocyanidins or proanthanols (e.g., grape seed extract), silymarin (e.g., milk thistle extract, Silybum marianum), ginkgo biloba, green tea polyphenols, and mixtures thereof. Carotenoids are powerful anti-oxidants, and they include beta-carotene, canthaxanthin, zeaxanthin, lycopen, lutein, crocetin, capsanthin, and the like. Indeed, any pharmaceutically acceptable compounds suitable for administration orally or topically may be used as an anti-oxidant in the compositions. Preferably, the anti-oxidant component includes Vitamin E, Vitamin C, or a carotenoid. The anti-oxidant component, when used, is present in an amount sufficient to inhibit or reduce the effects of free-radicals. The anti-oxidant component may be present in an amount from about 0.001 to 1 weight percent, preferably from about 0.01 to 0.5 weight percent of the composition.

The pharmaceutical compositions of the invention may also include one or more of a local analgesic or anesthetic, antiyeast agent, antiperspirant, antipsoriatic agents antiaging agents, antiwrinkles agent, sun screen and sun blocking agents, skin lightening agents, depigmenting agents, vitamins, hormones and retinoids. Particularly preferred are compositions further comprising a local analgesic or anesthetic to alleviate the pain and discomfort associated with inflammatory skin diseases. Local anesthetic include, but are not limited to, lidocaine.

The pharmaceutical compositions of the invention may further include one or more of an immuno-enhancer to stimulate the bodies immune system. A suitable immuno-enhancer useful in the compositions of the invention is Aldara (Immiquimod). The immuno-enhancer may be present in an amount from about 0.1 to 10 weight percent, preferably from about 0.5 to 5 weight percent of the composition.

The ranges of the components of the pharmaceutical composition may vary, but the active ingredients should be understood to add to 100 weight percent of the active pharmaceutical composition. The compositions may be prepared in high concentrations for administration to be removed shortly thereafter, as well as in lower concentrations that are safer for products that can remain in contact with the skin for longer times.

The present invention is further directed to a method of preventing, treating, or managing one or more inflammatory skin conditions. The methods of the invention comprise administering to apatient inneedthereof atherapeutically effective amount of the compositions of the invention.

The term "therapeutically effective amount," as used herein, means that amount of the pharmaceutical composition that provides a therapeutic benefit in the treatment, prevention, or management of one or more skin conditions.

The magnitude of a prophylactic or therapeutic dose of the composition in the acute or chronic management of inflammatory skin conditions will vary with the severity of the condition to be treated. The dose, and perhaps the dose frequency, will also vary according to the age, body weight, and response of the individual patient. In general, a preferred topical daily dose range, in single or divided doses, for the conditions described herein should be from about 1 mg to 20,000 mg, more preferably about 2,000 mg to 16,000 mg, and most preferably about 6,000 mg to 10,000 mg of the active components (i.e., excluding excipients and carriers).

Those of ordinary skill in the art will also understand that topical effectiveness of pharmaceuticals requires percutaneous absorption and bioavailability to the target site. Thus, the compositions and methods of the invention require penetration through the stratum corneum into the epidermal layers, as well as sufficient distribution to the sites targeted for pharmacologic action. Without wishing to be bound by theory it is believed that the presences of the hydrogen peroxide and the moisturizing agent facilitate penetration of the anti-inflammatory through the stratum corneum into the epidermal layers.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The pharmaceutical compositions used in the methods of the present invention include the active ingredients described above, and may also contain pharmaceutically acceptable carriers, excipients and the like, and optionally, other therapeutic ingredients.

Suitable dosage forms for topical administration include, but are not limited to, dispersions, lotions; creams; gels; pastes; powders; aerosol sprays; syrups or ointments on sponges or cotton applicators; and solutions or suspensions in an aqueous liquid, non-aqueous liquid, oil-in-water emulsion, or water-in-oil liquid emulsion. Because of its ease of administration, a cream, lotion, or ointment represents the most advantageous topical dosage unit form, in which case liquid pharmaceutical carriers may be employed in the composition. These creams, lotions, or ointments, may be prepared as rinse-off or leave-on products, as well as two stage treatment products for use with other skin cleansing or managing compositions. In a preferred embodiment, the compositions are administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

The compositions of the invention may be prepared by any of the methods of pharmacy, but all methods include the step of bringing into association the carrier(s) with the active ingredient, which constitutes one or more necessary ingredients. In general, the compositions are prepared by uniformly and intimately admixing the active ingredient with liquid carriers or finely divided solid carriers or both, and then, if necessary, shaping the product into the desired presentation.

Desirably, each unit dose, e.g., gel, cream, or ointment, contains from about 1 mg to 2,000 mg of the active ingredients, preferably about 200 mg to 1,600 mg, and more preferably about 600 mg to 1,000 mg of the composition.

The methods of the invention may further comprise administering one or more additional dermatological agents by a route of administration other than topically. Any suitable route of administration may be employed for providing the patient with an effective dosage of the additional component including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation and like forms of administration. Preferably, the additional component is administered orally.

Preferably, the additional component is a moisturizer or anti-inflammatory agents. Preferred moisturizers for oral administration include, but are not limited to, panthenol; primrose oil; GLA 3 and other fish oils that may include, for example, the omega-3 and omega-6 oils and/or linoleic acid; and flax seed oil. Preferred anti-inflammatory agents for oral administration include, but are not limited to, aspirin, ibuprofen, ketoprofen, andnaproxen. In another embodiment the additional component is an analgesic or anesthetic.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1

Skin Cleanser Formulation

A pharmaceutical composition according to the invention may be prepared for cleansing skin as set forth below:

|  | Ingredient | Trade Name/Supplier | % by Weight |
|---|---|---|---|
| Part A | Deionized Water | N/A | 49.2 |
|  | Trisodium Ethylene-Diamine-Tetraacetic Acid (EDTA) | HAMP-ENE $Na_3T$/Akzo Nobel | 0.2 |
|  | Sodium Laureth-13 Carboxylate | SURFINE WLL/Finetex | 10 |
|  | Disodium Laureth Sulfosuccinate | MACKANATE EL/McIntyre Group | 17 |
|  | Disodium Cocoamphodiacetate | MONATERIC CDX-38/Mona | 11 |
|  | PEG-150 Pentaerythrityl Tetrastearate | CROTHIX/Croda | 1.5 |
|  | PEG-150 Distearate | KESSCO PEG 6000 DS/Stepan | .7 |
|  | Methylparaben | N/A | 0.2 |
| Part B | Salicylic Acid | Salicylic Acid, powder, USP/Spectrum | 1.6 |
|  | Citric Acid | N/A | 1.5 |
|  | Triclosan | IRGASAN DP300/Ciba | 0.3 |
| Part C | PPG-26-Buteth-26, PEG-40 Hydrogenated Castor Oil | SOLUBILISANT LR1/Les Colorant Wackherr SA | 2 |
|  | Fragrance (Parfum) | Fragrance - BELL #J7393/Bell Flavors and Fragrances | 0.3 |
|  | Menthol | Menthol Crystals, USP | 0.1 |
| Part D | Butylene Glycol, Deionized water, Black Cohosh (Cimicifuga Racemosa) Extract | ACTIPHYTE OF BLACK SNAKEROOT BG50/Active Organics | 0.1 |
|  | Butylene Glycol, Deionized water, Camellia Oleifera Extract | ACTIPHYTE OF JAPANESE GREEN TEA BG50/Active Organics | 0.1 |
|  | Sodium Peroxylinecarbolic Acid (PCA) | AJIDEW-50/Ajinomoto | 0.2 |
|  | Cocamidopropyl PG-Dimonium Chloride Phosphate | PHOSPHOLIPID PTC/Mona | 1 |

-continued

| | Ingredient | Trade Name/Supplier | % by Weight |
|---|---|---|---|
| Part E | Hydrogen Peroxide | Hydrogen Peroxide, 35% solution, technical | 3 |
| | | | 100% |

HAMP-ENE Na₃T is commercially available from Akzo Nobel Inc. of Dobbs Ferry, NY; SURFINE WLL is commercially available from Finetex, Inc. of Elmwood Park, NJ; MACKANATE EL is commercially available from McIntyre Group of University Park, IL; MONATERIC CDX-38 and PHOSPHOLIPID PTC are commercially available from Mona Industries Inc. of Patterson, NJ; CROTHIX is commercially available from Croda Inc. of Parsippany, NJ; KESSCO PEG 600 DS is commercially available from Stepan Co. of Northfield, IL; IRGASAN DP300 is commercially available from Ciba Specialty Chemicals Corp. of Albemarle, NC; SOLUBILISANT LR1 is commercially available from Les Colorant Wackherr SA of St. Ouen L'Aumone, France; BELL #J7393 is commercially available from Bell Flavors and Fragrances of Northbrook, IL; ACTIPHYTE OF BLACK SNAKEROOT BG50 and ACTIPHYTE OF JAPANESE GREEN TEA BG50 are commercially available from Active Organics of Dallas, TX; and AJIDEW –50 is commercially available from Ajinomoto USA Inc. of Teaneck, NJ.

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 4.5 and a viscosity between 3,000 to 4,000 cps (RVT: #4@10 rpm@25° C.).

Example 2

Advanced Acne Prone Skin Formulation

A pharmaceutical composition according to the invention may be prepared for treating skin prone to acne as set forth below:

| | Ingredient | Trade Name/Supplier | % by Weight |
|---|---|---|---|
| Part A | Deionized Water | N/A | 46.7 |
| | Hydroxyethylcellulose | CELLOSIZE QP52,000H/Amerchol | 1 |
| Part B | Tetrasodium Ethylene-Diamine-Tetraacetic Acid (EDTA) | HAMP-ENE 220/Akzo Nobel | 0.1 |
| | Butylene Glycol | 1,3-butylene glycol/Ashland | 5 |
| | Aloe Barbadensis Gel | Aloe Vera Freeze Dried Powder 200:1/Aloe | 0.1 |
| | Methyl Gluceth-10 | GLUCAM E-10/Amerchol | 3 |
| | Witch Hazel (*Hamamelis Virginiana*) Distillate | Witch Hazel Distillate, 14% | 3 |
| | Zinc Acetate | Zinc Acetate, crystals, USP/FCC | 0.5 |
| | Orange (*Citrus Aurantium Dulcis*) ExtractMethylparaben | NATURAL ORANGE EXTRACT #71689/Flavurence | 0.3 |
| | Dipotassium Glycyrrhizate | N/A | 0.3 |
| | Lecithin, Tocopherol and Magnesium Ascorbyl Phosphate | OXYSOMES/Barnett | 0.3 |
| | Palmitoyl Hydroxypropyltrimonium Amylopectin/Glycerin Crosspolymer, Lecithin, Grape (*Vitis Vinifera*) Seed Extract | GLYCOSPHERE PCO/Kobo | 0.2 |
| | Palmitoyl Hydroxypropyltrimonium Amylopectin/Glycerin Crosspolymer, Lecithin, *Camellia Sinensis* Extract | GLYCOSPHERE GT/Kobo | 0.5 |
| | *Epilobium Angustifolium* Extract | Canadian Willowherb Whole Extract (5% in water)/Fytokem | 0.5 |
| | Butylene Glycol and Water and *Arnica Montana* Extract | ACTIPHYTE OF ARNICA BG50/Active Organics | 0.5 |
| Part C | Alcohol (denatured) | SD Alcohol 40-B, Anhydrous/ | 20 |
| | Salicylic Acid | Salicylic Acid, powder, | 1 |

-continued

|  | Ingredient | Trade Name/Supplier | % by Weight |
|---|---|---|---|
|  | Triclosan | USP/FCC/Spectrum IRGASAN DP300/Ciba | 0.4 |
| Part D | PPG-5-Ceteth-20 | PROCETYL AWS/Croda | 1 |
|  | PEG-40 Hydrogenated Castor Oil | CREMOPHOR RH-40/BASF | 0.6 |
|  | Retinol and Polysorbate 20 | RETINOL 50C/BASF | 0.1 |
|  | Phytonadione | N/A | 0.1 |
|  | Linoleic Acid | EMERSOL 315/Henkel | 0.3 |
| Part E | Glycolic Acid | GLYPURE = 70% Glycolic Acid/DuPont | 9 |
| Part F | Deionized water | N/A | 2 |
|  | Sodium Hydroxide | Sodium Hydroxide, pellets, USP/NF | 2 |
| Part G | Hydrogen Peroxide | Hydrogen Peroxide, 35% solution, technical | 1.5 |
|  |  |  | 100% |

CELLOSIZE QP52,000H and GLUCAM E-10 are commercially available from Amerchol Corp. of Edison, NJ; HAMP-ENE 220 is commercially available from Akzo Nobel Inc. of Dobbs Ferry, NY; Aloe Vera Freeze Dried Powder 200:1 is commercially available from Aloe Corp. of TX; OXYSOMES is commercially available from Barnet Products Corporation of Englewood Cliffs, NJ; Canadian Willowherb Whole Extract (5% in water) is commercially available from Fytokem, Inc. of Saskatoon, SK CANADA; GLYCOSPHERE PCO and GLYCOSPHERE GT are commercially available from Kobo Products Inc. of South Plainfield, NJ; ACTIPHYTE OF ARNICA BG50 is commercially available from Active Organics of Dallas, TX; PROCETYL AWS is commercially available from Croda Inc. of Parsippany, NJ; CREMOPHOR RH-40 and RETINOL 50C are commercially available from BASF Corporation of Budd Lake, NJ; GLYPURE = 70% Glycolic Acid is commercially available from DuPont of Wilmington, DE; EMERSOL 315 is commercially available from Henkel Corp. of Hoboken, NJ.

Deionized water was metered into the processing tank and mixing subsequently begun. CELLOSIZE QP52,000H was sprinkled in, heated to 70° C., and mixed until clear and uniform. The mixture was cooled to 40° C. Part B ingredients were added in the order above, with sufficient mixing after each ingredient was added. The mixture was cooled to 25° C. and premixed Part C ingredients were added and mixed until uniform. In a separate tank, Part D was heated to 40° C. until the solids were dissolved and then added to the batch of Parts A, B, and C. The mixture was mixed until uniform, then Part E was added and mixed until uniform. Premixed Part F was slowly added in increments as needed to obtain the desired pH of 3.3 to 3.8 at 25° C., then Part G was added and mixed until completely uniform. This resulted in a straw-colored, clear to slightly hazy, slightly viscous liquid having a pH @ 25° C. of 3.3 to 3.8 and a viscosity between 400 to 800 cps (RVT: #2@10 rpm@25° C.).

Example 3

Skin Perfecting Lotion

A pharmaceutical composition according to the invention may be prepared for treating skin as set forth below:

|  | Ingredient | Trade Name/Supplier | % by weight |
|---|---|---|---|
| Part A | Water (Aqua) | Deionized water | 60.6 |
|  | Carbomer | CARBOPOL ULTREZ 10/B.F. Goodrich | 0.3 |
|  | Sclerotium Gum | AMIGEL/Tri-K | 0.6 |
|  | Glycerin | Glycerin 99.5%/Ashland | 6.0 |
|  | Butylene Glycol | 1,3-butylene glycol/Ashland | 6.0 |
|  | Allantoin | Allantoin/ISP | 0.6 |
|  | Panthenol | DEXPANTHENOL/Roche | 0.6 |
|  | Tetrasodium EDTA | HAMP-ENE 220/Akzo | 0.2 |
|  | Methylparaben | Methylparaben/Ueno | 0.3 |
|  | Sodium PCA | AJIDEW-50/Ajinomoto | 0.5 |
| Part B | Dicapryl Maleate | BERNEL ESTER DCM/Bernel | 6.0 |
|  | Squalene | PHYTOLANE/Barnet | 0.8 |
|  | Sorbitan Stearate | ARLACEL 60/ICI | 1.5 |
|  | Stearic Acid | EMERSOL 132/Henkel | 1.3 |
|  | Dimethicone | DOW CORNING 200, 350 cs./Dow Coming | 0.8 |
|  | C12-C15 Alkyl Benzoate | FINSOLV TN/Finetex | 3.0 |
|  | Cetearyl Alcohol and Ceteareth | HEXOTOL D/Heterene | 0.6 |
|  | Propylparaben | Propylparaben/Ueno | 0.2 |
| Part C | Water (Aqua) | Deionized water | 0.3 |
|  | Triethanolamine | Triethanolamine 99%/Ashland | 0.3 |
| Part D | Orange (Citrus Aurantium | NATURAL ORANGE | 0.3 |

-continued

| Ingredient | Trade Name/Supplier | % by weight |
|---|---|---|
| *Dulcis*) Extract | EXTRACT #71689/Flavurence | |
| Diazolidinyl Urea | GERMALL II/ISP | 0.3 |
| Glycolipids and Hyaluronic Acid | PHYTO/CER HA/Tri-K | 0.3 |
| Palmitoyl Hydroxypropyltrimonium Amylopectin/Glycerin Crosspolymer and Lecithin and grape (*Vitis Vinifera*) Seed Extract | GLYCOSPHERES PCO/Kobo | 0.3 |
| Palmitoyl Hydroxypropyltrimonium Amylopectin/Glycerin Crosspolymer and Lecithin and *Camellia Sinensis* Extract | GLYCOSPHERES GT/Kobo | 0.3 |
| Propylene Glycol | Propylene Glycol/Ashland | 0.6 |
| Algae Extract | HAWAIIAN SEAPLANT EXTRACT-J/Tri-K | 0.2 |
| Lecithin and Tocopherol and Magnesium Ascorbyl Phosphate | OXYSOMES/Barnet | 0.6 |
| Butylene Glycol and Honey Extract (Mel) and Meadowsweet (*Spiraea Ulmaria*) Extract | ACTIPLEX 1072/Active Organics | 1.1 |
| Talc and C9-C13 Fluoroalcohol and Phosphoric Acid | PF-5 TALC JA-46R/Kobo | 0.8 |
| Hydrolyzed Soy Flour | RAFFERMINE/R.I.T.A. | 0.3 |
| Oat (*Avena Sativa*) Protein | REDUCTINE/R.I.T.A. | 0.3 |
| Phytonadione | Phytonadione/Roche | 0.01 |
| Retinol and Polysorbate 20 | RETINOL 50C/BASF | 0.1 |
| *Epilobium Angustifolium* Extract | Canadian Willowherb Whole Extract (5% in water)/Fytokem | 0.5 |
| *Arnica Montana* Extract | ACTIPHYTE OF ARNICA BG50/Active Organics | 0.5 |
| Part E Hydrogen Peroxide | Hydrogen Peroxide, 35% solution, technical | 3 |
| | | 100.0 |

CARPOL ULTREZ 10 is commercially available from B.F. Goodrich Co. of Richfield, OH; AMIGEL, PHYTO/CER and HAWAIIAN SEA PLANT EXTRACT are available from Tri-K-Chemical of Fairview, MT; Allantoin and GERMALL II are available from ISP Chemicals Inc. of Calvert City, KY; DEXPANTHENOL and Phytonadione are available from Roche Holdings, Inc. of Wilmington, DE; Methylparaben and Propylparaben are commercially available from Ueno Fine Chemicals Inc. of New York, NY AJIDEW N-50 is commercially available from Ajinomoto USA Inc. of Teaneck, NJ; BERNEL ESTER is commercially available from Bernel Chemical Co. of Englewood, NJ; PHYTOLAINE is commercially available from Barnet Products Corporation of Englewood Cliffs, NJ; ARLACEL 60 is commercially available from ICI Americas Inc. of Wilmington, DE; EMERSOL 132 is commercially available from Henkel Corp. of Hoboken, NJ; DOW CORNING 200, 350 cs. is commercially available from Dow Corning Corp. of Auburn, MI; FINSOLV TN is commercially available from Finetex Inc. of Elmwood Park, NJ; HETOXOL D is commercially available from Heterene Chemical Co. of Paterson, NJ; NATURAL ORANGE EXTRACT #71689 is commercially available from Flavurence Corp. of Annandale, NJ; ACTIPLEX 1072 is commercially available from Active Organics Inc. of Lewisville, TX; PF-5 TALC JA-46R is commercially available from Kobo Products Inc. of South Plainfield, NJ; RAFFERMINE and REDUCTINE are commerically available from RITA Chemical Corp of East Northport, NY.

The Skin Perfecting Lotion was prepared by metering deionized water into a processing tank and mixing at high speed. CARBOPOL ULTREZ 10 was sprinkled in. When the CARBOPOL ULTREZ 10 was completely dispersed, AMIGEL was added and the mixture mixed until smooth and uniform. The mixture was heated to 80° C., the remaining Part A ingredients were added, and then mixed until uniform. In a separate tank, the Part B ingredients were combined and heated to 80° C. until all the solids were completely dissolved. Part B was added to Part A and the resulting batch was mixed until uniform. Premixed Part C was added and the batch mixed until homogeneous. The batch was cooled to 40° C. and the Part D ingredients were added and mixing continued until the temperature of the mixture was 35° C. The resulting Skin Perfecting Lotion was a light beige, opaque, viscous lotion having a pH at 25° C. of 6.2 to 7.2 and a viscosity of 14,000 to 24,000 cps. (RVT: #5@10 rpm@25° C.).

Example 4

Acne Management Formula

A pharmaceutical composition according to the invention may be prepared for managing acne as set forth below:

|        | Ingredients | Trade Name/Supplier | % by weight |
|--------|-------------|---------------------|-------------|
| Part A | Water (Aqua) | Deionized Water | 55.3 |
|        | Sclerotium Gum | AMIGEL/Alban Muller | 0.4 |
|        | Disodium EDTA | HAM-ENE NA$_2$/Akzo | 0.3 |
|        | Allantoin | Allantoin/ISP | 0.2 |
|        | Methylparaben | Methylparaben/Ueno | 0.3 |
|        | Zinc Oxide | 66 ZINC OXIDE U.S.P./Whitaker, Clark & Daniels | 0.3 |
| Part B | Water (Aqua) | Deionized Water | 10 |
|        | Hydrolyzed Oat Flour and Oat Betaglucan | RITAVENA 5/R.I.T.A. | 2.8 |
|        | Dicaprylyl maleate | BERNEL ESTER DCM/Bernel | 3 |
|        | Glycerayl Stearate and PEG-100 Stearate | ARLACEL 165/ICI | 3 |
|        | Cetearyl Alcohol and Ceteareth-20 | HEXOTOL D/Heterene | 3 |
|        | Propylparaben | Propylparaben/Ueno | 0.1 |
| Part D | Salicylic Acid | Salicylic Acid, powder, U.S.P.-N.F./Spectrum | 1.3 |
|        | Sulfur | Sulfur, precipitated, U.S.P.-N.F./Spectrum | 6.5 |
| Part E | Water (Aqua) | Deionized Water | 3 |
|        | Sodium Hydroxide | Sodium Hydroxide, pellets, U.S.P.-N.F./Spectrum | 0.1 |
|        | Glycolic Acid | GLYPURE 70% GLYCOLIC ACID/DuPont | 6.5 |
| Part F | Orange (*Citrus Aurantium Dulcis*) Extract | ORANGE EXTRACT PRODUCT #61522/Sunkist | 1.1 |
|        | Diazolidinyl Urea | GERMALL II/ISP | 0.4 |
|        | Dipotassium Glycyrrhizate | Dipotassium Glycyrrhizinate/Int'l Sourcing | 0.3 |
|        | Lecithin and Tocopherol and Magnesium Ascorbyl Phosphate | OXYZOMES/Barnett | 0.3 |
|        | Palmitoyl Hydroxypropyltrimonium Amylopectin/Glycerin Crosspolymer and Lecithin and Grape (*Vitis Vinifera*) Seed Extract | GLYCOSPHERES PCO/Kobo | 0.3 |
| Part G | Hydrogen Peroxide | Hydrogen Peroxide, 35% solution, technical | 1.5 |
|        |             |                     | 100.0 |

AMIGEL is commercially available from Alban Muller International of Vincennes, France; HAM-ENE NA$_2$ is commercially available from Akzo Chemicals Inc. of Deer Park, TX; 66 ZINC OXIDE U.S.P. is commercially available from Whitaker, Clark & Daniels of South Plainfield, NJ; Salicylic Acid, powder, U.S.P.-N.F., Sulfur, precipitated, U.S.P.-N.F. and Sodium Hydroxide, pellets, U.S.P.-N.F. are commercially available from Spectrum Mfg. Corp of New Brunswick, NJ; ORANGE EXTRACT PRODUCT #61522 is commercially available from Sunkist Growers, Inc. of Van Nuys, CA; Dipotassium Glycyrrhizinate is commercially available from International Sourcing Inc. of Upper Saddle River, NJ.

The Acne Management Formula was prepared by metering deionized water into a processing tank and mixing at high speed. AMIGEL was sprinkled in. When the AMIGEL was completely dispersed, the mixture was heated to 85° C. and the remaining Part A ingredients were added and the mixture mixed well after each addition. In a separate tank, Part B was heated to 100° C., mixed until smooth, cooled to 80° C. and added to the batch. The resulting batch was mixed well. In another tank, the Part C ingredients were heated to 75° C. When all the solids dissolved, Part C was added to the batch, the batch was mixed until smooth and uniform, and the batch cooled to 50° C. Part D ingredients were added to the batch, the batch was homogenized for 5 to 10 minutes until the batch was smooth and uniform, and the batch was cooled to 40° C. The deionized water of part E was premixed with the sodium hydroxide pellets and the resulting solution was mixed well until all solids were dissolved. While mixing the solution, glycolic acid was slowly added in increments and the solution was mixed until homogeneous. The solution was added to the batch and the Part F ingredients were added to the batch. The batch was mixed and cooled to 35° C. The Acne Management Formula was a light yellow, opaque smooth lotion having a pH at 25° C. of 3.8 to 4.8 and a viscosity of 10,000 to 20,000 cps. (RVT: #5@10 rpm@25° C.).

Example 5
Clarifying Skin Cleanser

A pharmaceutical composition according to the invention may be prepared for managing acne as set forth below:

|  | Ingredients | Trade Name/Supplier | % by weight |
|---|---|---|---|
| Part A | Water (Aqua) | Deionized Water | 48.5 |
|  | Sodium Lauroyl Oat Amino Acid | PROTEOL O.A.T./Seppic | 2 |
|  | Decyl Glucoside | ORAMIX NS-10/Seppic | 3 |
|  | Cocamidopropyl Betaine | AMPHOSOL CA/Stephan | 12.5 |
|  | Disodium Laureth Sulfosuccinate | MACKANATE EL/McIntyre | 24 |
|  | PEG-120 Methyl Glucose Dioleate | GLUCAMATE DOE-120/Amerchol | 3.5 |
|  | Methylparaben | Methylparaben/Ueno | 0.2 |
|  | PEG-150 Pentaerythrityl Tetrastearate | CROTHIX/Croda | 0.25 |
| Part B | Salicylic Acid | Salicylic Acid, powder, USP/Spectrum | 2 |
|  | Tetrasodium EDTA | HAMP-ENE-100/Akzo | 0.3 |
|  | Triclosan | IRGASAN D300/Ciba Specialty Chemicals | 0.2 |
| Part C | PPG-26-Buteth-26 and PEG 40Hydrogenated castor Oil | SOLUBILISANT LRI/ Whittaker, Clark & Daniels | 2 |
|  | Fragrance | Fragrance-BELL #J7393/ Bell | 0.3 |
|  | Menthol | Menthol Crystals, USP/ Spectrum | 0.1 |
| Part D | Butylene Glycol and water (aqua) and Black Cohosh (*Cimicifuga Racemosa*) Extract | ACTIPHYTE OF BLACK SNAKEROOT BG50/Active Organics | 0.2 |
|  | Butylene Glycol and water (aqua) and *Camellia Oleifera* Extract | ACTIPHYTE OF JAPANESE GREEN TEA BG50/Active Organics | 0.2 |
|  | Sodium PCA | AJIDEW N-50/Ajinomoto | 0.4 |
|  | Imidazolidinyl Urea | GERMALL 115/ISP | 035 |
|  |  |  | 100.0 |

PROTEAL O.A.T. is commercially available from Seppic Inc. of Fairfield, NJ; AMPHOSOL CA is commercially available from Stephan Co. Inc. of Fort Lauderdale, FL; GLUCAMATE DOE-120 is commercially available from Amerchol Corp. of Edison, NJ; HAMPENE-100 is commercially available from Akzo Nobel Inc. of Dobbs Ferry, NY; SOLUBILISANT LRI is commercially available from Whitaker, Clark & Daniels of South Plainfield, NJ; GERMALL 115 is commercially available from ISP Chemicals Inc. of Calvert City, KY.

The Clarifying Skin Cleanser was prepared by metering deionized water into a processing tank, mixing, and heating to 75° C. The part A ingredients were added and mixed until all the solids dissolved. The resulting mixture was cooled to 60° C. In a separate vessel the Part B ingredients were combined. The Part B ingredients were then added to Part A and the resulting batch was mixed until uniform. The resulting mixture was cooled to 50° C. In a separate vessel the Part C ingredients were mixed until uniform. The part C ingredients were added to the batch and the resulting batch was mixed until uniform. The batch was cooled to 40° C. and the part D ingredients were added and mixing continued until uniform followed by cooling to 30° C. The Clarifying Skin Cleanser Formula was a pale yellow, slightly viscous liquid having a pH at 25° C. of 4.5 to 5.5 and a viscosity of 5,000 to 9,000 cps. (RVT: #@10 rpm@25° C.).

Example 6

Antimicrobial Effectiveness of the Invention— Advanced Acne Prone Skin Formulation Culture Preparation

*Escherichia coli* (ATCC # 8739), *Staphylococcus pureus* (ATCC #6533), *Pseudomonas aeruginosa* (ATCC #9027) were each propagated in Trypicase Soy Broth (TSB) at 35° C. for 24 hrs. *Candida albicans* (ATCC #10231), and *Aspergillus niger* (ATOC # 16404) were propagated in Yeast and Mold Broth (YM) at 24° C. for 72 h. One loop of each bacteria culture was streaked onto Trypticase Soy Agar (TSA) and the yeast and mold onto Sabouraud Dextrose Agar (SDA). The bacterial and yeast cultures were incubated for 24 h at 35° C. and 48 h at 24° C., respectively. The mold culture was incubated for 5 days at 24° C. Following appropriate incubation, the surface growth of the organisms were washed with sterile Saline TS. Additional saline was added to reduce the microbial count. Each respective cell suspension was further diluted with sterile saline TS to an appropriate concentration.

Product Inoculation

Five 20-g portions of the Advanced Acne Prone Skin Formula of Example 2 was aseptically placed into sterile bottles. Each bottle was independently inoculated with 0.1 mL of the inoculum suspension.

Target Inoculation Concentration

A final concentration of $10^5$ and $10^6$ cfu/g of product was obtained. This spike suspension was assayed for each respective organism to determine the initial microbial load in the product. All enumeration analyses were performed by preparing serial 10-fold dilutions in Butterfield's Phosphate Buffered Diluent (BPBD), and then plated using the pour plate technique on respective media.

Test Intervals

An enumeration of the target organisms were performed on each inoculum. Immediately after inoculation (less than 1 minute), each product was assayed to determine the density of viable target organisms according to the pour plate technique. Each sample was tested again after 2 and 4 minutes. A 1-g portion was removed and mixed with 9.9 mL of BPBD. Serial dilutions were prepared as appropriate. Test samples containing bacterial cultures were plated with TSA and incubated for 48 h at 35° C. Samples containing yeast and mold were plated with SDA and incubated for 5 days at 24° C.

Results

The following results were obtained for each of the five organisms.

| Testing Schedule (Time: minutes) | Recovery Levels (cfu/g) Advanced Acne Prone Skin Formula |
|---|---|
| Test Organism: *Candida albicans* (ATOC # 10231) Theoretical Inoculum Level: 400,000 cfu/g | |
| 0 (less than 1) | <10 |
| 2 | <10 |
| 4 | <10 |
| Test Organism: *Aspergillus niger* (ATCC # 16404) Theoretical Inoculum Level: 160,000 cfu/g | |
| 0 (less than 1) | <10 |
| 2 | <10 |
| 4 | <10 |
| Test Organism: *Escherichia coli* (ATCC # 8739) Theoretical Inoculum Level: 1,000,000 cfu/g | |
| 0 (less than 1) | <10 |
| 2 | <10 |
| 4 | <10 |
| Test Organism: *Staphylococcus aureus* (ATCC # 6538) Theoretical Inoculum Level: 700,000 | |
| 0 (less than 1) | <10 |
| 2 | <10 |
| 4 | <10 |
| Test Organism: *Pseudomonas aeruginosa* (ATCC # 9027) Theoretical Inoculum Level: 260,000 | |
| 0 (less than 1) | <10 |
| 2 | <10 |
| 4 | <10 |

Discussion and Conclusion

The Advanced Acne Prone Skin Formulation prepared according to the present invention exhibited excellent antimicrobial properties. In less than one minute there was greater than a 99.99% reduction in levels of *Candida albicans, Escherichia coli, Staphylococcus aureus, Pseudomonas aeruginosa,* and *Aspergillus niger.*

Example 7

Antimicrobial Effectiveness of Another Formulation of the Invention—Clarifying Skin Cleanser Culture Preparation

*Escherichia coli* (ATCC # 8739), *Staphylococcus pureus* (ATCC # 6533), and *Pseudomonas aeruginosa* (ATCC #9027) were propagated in Trypicase Soy Broth (TSB) at 35° C. for 24 h. *Candida albicans* (ATCC # 10231) and *Aspergillus niger* (ATOC # 16404) were propagated in Yeast and Mold Broth (YM) at 24° C. for 72 h. One loop of each bacteria culture was streaked onto Trypticase Soy Agar (TSA) and the yeast and mold onto Sabouraud Dextrose Agar (SDA). The bacterial and yeast cultures were incubated for 24 h at 35° C. and 48 h at 24° C., respectively. The mold culture was incubated for 5 days at 24° C. Following appropriate incubation, the surface growth of the organisms were washed with sterile Saline TS. Additional saline was added to reduce the microbial count. Each respective cell suspension was further diluted with sterile saline TS to an appropriate concentration.

Product Inoculation

Five 20-g portions of the Clarifying Skin Cleanser of Example 1 was aseptically placed into sterile bottles. Each bottle was independently inoculated with 0.1 mL of the inoculum suspension.

Target Inoculation Concentration

A final concentration of $10^5$ and $10^6$ cfu/g of product was obtained. This spike suspension was assayed for each respective organism to determine the initial microbial load in the product. All enumeration analyses were performed by preparing serial 10-fold dilution's in Butterfield's Phosphate Buffered Diluent (BPBD), and then plated using the pour plate technique on respective media.

Test Intervals

An enumeration of the target organisms were performed on each inoculum. Immediately after inoculation (less than 1 minute), each product was assayed to determine the density of viable target organisms according to the pour plate technique. Each sample was tested again after 2 and 4 minutes. A 1-g portion was removed and mixed with 9.9 mL of BPBD. Serial dilutions were prepared as appropriate. Test samples containing bacterial cultures were plated with TSA and incubated for 48 h at 35° C. Samples containing yeast and mold were plated with SDA and incubated for 5 days at 24° C.

Results

The following results were obtained for each of the five organisms.

| Testing Schedule (Time: minutes) | Recovery Levels (cfu/g) Clarifying Skin Cleanser |
|---|---|
| Test Organism: *Candida albicans* (ATOC # 10231) Theoretical Inoculum Level: 400,000 cfu/g | |
| 0 (less than 1) | 25,000 |
| 2 | 20,000 |
| 4 | 14,000 |
| Test Organism: *Aspergillus niger* (ATCC # 16404) Theoretical Inoculum Level: 160,000 cfu/g | |
| 0 (less than 1) | 1,400 |
| 2 | 1,200 |
| 4 | 1,000 |
| Test Organism: *Escherichia coli* (ATCC # 8739) Theoretical Inoculum Level: 1,000,000 cfu/g | |
| 0 (less than 1) | <10 |
| 2 | <10 |
| 4 | <10 |
| Test Organism: *Staphylococcus aureus* (ATCC # 6538) Theoretical Inoculum Level: 700,000 | |
| 0 (less than 1) | <10 |
| 2 | <10 |
| 4 | <10 |
| Test Organism: *Pseudomonas aeruginosa* (ATCC # 9027) Theoretical Inoculum Level: 260,000 | |
| 0 (less than 1) | <10 |
| 2 | <10 |
| 4 | <10 |

Discussion and Conclusion

The Clarifying Skin Cleanser exhibited excellent antimicrobial properties. In less than one minute there was a >99.99% reduction in levels of *Escherichia coli, Staphylococcus aureus,* and *Pseudomonas aeruginosa.* In less than one minute, levels of *Aspergillus niger* and *Candida albicans* were reduced by 99.1% and 94.0%, respectively.

Example 8

Irritation Test Using the Invention

Irritation potential following epidermal contact by compositions prepared according to the invention was examined. Fifty-three subjects ranging from 18 to 77 were evaluated. The patients were administered 0.2 mL, or an amount sufficient to cover the upper back between the scapulae, of a 10 percent dilution of the formulation used in Example 2. The administration occurred by applying the composition to a 1"×¾" absorbent pad portion of an adhesive dressing, which was secured to the treatment site on each patient. The test material remained in contact for a total of 48 hours, and the test sites were evaluated at that time and at 72 hours (24 hours later) for changes using a 6-point scale ranging from no visible skin reaction up to severe erythema, possible edema, vesiculation, bullae and/or ulceration. One test subject did not complete the study. Observations indicated negative irritation throughout the test interval, i.e. no visible skin reaction on a single patient.

Example 9

Hydrogen Peroxide Stability Test

The formulations prepared according to Examples 1 of the invention having hydrogen peroxide, citric acid, salicylic acid, an antibacterial agent, and an amphoteric 2 surfactant were heated to between 40° C. to 45° C. for three months in an oven test. The oxygen content of the formula which was assayed after the stability test, showed no more than 3 weight percent loss of the original hydrogen peroxide content. Such high stability provides an improved composition having a long shelf-life without substantial loss of efficacy.

Examples 10–12

Acne Treatment Regimen

An acne treatment regimen comprising Clarifying Cleanser, Advanced Acne Prone Skin Formula, Skin Perfecting Lotion and Acne Management Formula (Examples 1, 2, 3, and 4, respectively) was administered to 15 subjects. Subjects were evaluated after 2 weeks and 4 weeks use of the treatment regimen. Subjects were evaluated for total facial lesions, skin hydration and overall appearance of acne.

Testing of the Treatment Regimen

The acne treatment regimen comprising a ADVANCED ACNE PRONE SKIN FORMULA, SKIN PERFECTING LOTION, ACNE MANAGEMENT FORMULA, and CLARIFYING SKIN CLEANSER, prepared according to Examples 2,3,4, and 5, respectively, was administered to 15 subjects who exhibited a Grade 2–4 acne condition according to the grading scale provided below:

0: Facial skin need not be perfectly clear. A few scattered comedones or papules may be present, but these should be visible only on close examination.

2: About one fourth of facial area is involved, with small papules and large or small comedones. A few pustules or large prominent papules may be present.

4: About half of facial area is involved, with small papules and large or small comedones. A few pustules or large prominent papules are usually present. (If lesions are large, subject may have Grade 4 severity, although less than half of facial area is involved).

6: About three-fourths offacial area is involved, with papules and/or large open comedones. (Lesser facial area of involvement is permissible if inflammatory lesions are large) numerous pustules are usually present, some of which may be large.

8: Practically all of facial area is involved, with lesions. Large prominent pustules are usually visible. Lesions are usually highly inflammatory. Other types of acne (such as conglobata, including sinus and cystic types).

On the first day of the study all subjects were acclimated to ambient temperature and relative humidity for fifteen minutes. After the equilibration period, a trained technician examined each subject's face and recorded the number of inflammatory and non-inflammatory lesions in each of six sections of the face. The lesions of the six sections were totaled to obtain a global assessment score for each subject. Clinical photographs were taken in various poses for each subject and three Corneometer measurements were taken.

Subjects were provided with the treatment regimen and were given the following instructions for the treatment regimen:

CLARIFYING CLEANSER: Apply twice per day (once in the morning and once in the evening). Pour a small amount into hand or wash cloth. Apply to dampened face and neck. Massage gently into full lather. Rinse thoroughly with warm water and pat dry. Follow with ACNE PRONE SKIN FORMULA.

ACNE PRONE SKIN FORMULA: Apply after cleansing twice per daily (once in the morning and once in the evening). Apply a small amount to face and neck or areas affected with acne. Follow with SKIN PERFECTING LOTION.

SKIN PERFECTING LOTION: Use twice per day after cleansing and treating skin. Apply a small amount to face and neck.

ACNE MANAGEMENT FORMULA: Use twice a day after using CLARIFYING CLEANSER, ACNE PRONE SKIN FORMULA, and SKIN PERFECTING LOTION. Apply a small amount to affected area to spot treat.

Subjects were required to maintain a daily diary indicating date, time of use and comments. Subjects were permitted to use their customary make-up products during the study. However, subjects were instructed not to introduce any new cosmetic or facial treatment products during the study. Following the two week test material use period subjects were evaluated for an interim count of total facial lesions, Corneometer readings and clinical photographs. After four weeks of test material use subjects returned with their diaries for a final lesion count, Corneometer readings and clinical photographs. Standard paired t-tests were used to determine statistically significant differences between baseline and two (2) and four (4) week total facial lesion counts and Corneometer readings. Statistical significance exists for all p-values less than or equal to 0.05 at the 95% confidence level. Improvement scores for the appearance of acne in clinical photographs were analyzed using Z-tests.

A total of fourteen subjects finished the study. One subject was disqualified immediately for lack of compliance with the Inclusion Criteria of the protocol. A review of the daily diaries indicated that four (4) subjects reported redness, burning, stinging and/or "irritation" during the study period. One (1) of the subjects reported the onset of redness and burning on day five (5) of the study immediately after product application and lasting for fifteen (15) to twenty (20) minutes. The subject was instructed to discontinue test material use on day ten (10) of the study. On day fourteen (14) the subject was examined by a doctor and no evidence of skin irritation was observed. The subject was instructed to begin use of the treatment material at this time. The subject reported no evidence of irritation until day twenty four (24) of the study and completed study participation. No evidence of irritation was observed at the final visit. The subjects reaction was diagnosed as dermatitis. The remaining subjects reported symptoms following one (1) to two (2) uses of the test material and completed study participation without further complaints.

Example 10

Total Lesion Count Following Treatment Regimen

The acne present on the skin of each subject was evaluated by visual examination using the grading scale described herein. The number of lesions on the face were counted at each visit. The number of open and closed comedones, as well as papules and pustules, were recorded. A global assessment score, the total of all lesions, was recorded for each visit. Reductions in the global assessment score are indicative of a reduced incidence and/or severity of acne lesions. The data for total lesion count is provided below.

| | Total Lesion Count | | |
|---|---|---|---|
| | Baseline | 2 Weeks | 4 Weeks |
| Mean | 44.4 | 33.4 | 27.6 |
| Mean Percent Difference from Baseline | | −26% | −40% |
| σ | | 30% | 22% |

The regimen showed a statistically significant decrease of twenty-six percent (26%) in the number of lesions observed after using the treatment regimen for two (2) weeks and a statistically significant decrease of forty (40%) after using the treatment regimen for four (4) weeks compared to baseline (p=0.02 and p=1.07 E-05, respectively).

Example 11

Photographic Evaluation Following Treatment Regimen

Photographs of subjects were taken at designated visits using the Canfield Clinical System of imaging equipment. This particular system permits comparison of photographs to be made with the confidence that the only factors which may have changed are those resulting from treatment. This is achieved by precisely and reproducibly positioning the head of the subject and carefully controlling the lighting, film type and processing. Photographs were visually assessed and evaluated by a trained technician before and after use of the test material. The following scoring scale was used for visual assessment of the skin:

Improvement scores for the appearance of acne in clinical photographs were analyzed using Z-tests. For the two (2) and four (4) week scores, the number of subjects exhibiting improvements scoring a two (2), three (3), four (4) or five (5) was compared to the number of subjects exhibiting no improvement, scored as a one (1). The improvement assessment of the overall appearance of acne, rated from clinical photographs, is provided below.

| | Photographic Evaluation | | | | | |
|---|---|---|---|---|---|---|
| | Score: | 1 | 2 | 3 | 4 | 5 |
| Week 2 | Number of Subjects Assigned each Score | 5 | 5 | 2 | 2 | 0 |
| | Percentage | 35.7% | | 64.3% | | |
| | Z-Score | | | −1.12 | | |
| Week 4 | Number of Subjects Assigned each Score | 4 | 4 | 5 | 1 | 0 |
| | Percentage | 28.6% | | 71.4% | | |
| | Z-Score | | | −1.77 | | |

1 = no improvement
2 = slight improvement
3 = mild improvement
4 = moderate improvement
5 = extreme improvement The number of subjects exhibiting improvement from baseline in the overall appearance of acne at two (2) weeks was greater than subjects with no improvement. The Z-score obtained at two (2) weeks corresponds to improved skin appearance having a statistical significance at a 74% confidence level. In the four (4) week photograph the number of subjects exhibiting improvement from baseline in the overall appearance of acne was greater than subjects with no improvement. The Z-score obtained at four (4) weeks corresponds to improved skin appearance having statistical significance at a 92% confidence level.

Example 12

Moisturization via Corneometer Following Treatment Regimen

Changes in skin hydration were measured with a CORNEOMETER which is a commercially available instrument (CM-820, Courage and Khazaka Germany) designed to measure changes in the capacitance of the skin resulting from small changes in the degree of hydration. The CORNEOMETER expresses the capacitance of the skin in arbitrary unit of skin hydration (H). The instrument is capable of measuring the moisture of the stratum corneum to a depth of 0.1 mm and is used to measure the effects of cosmetic preparations on the moisture content of the skin. Tests using the CORNEOMETER were conducted by taking 3 measurements, one at the right and left cheek and one at the center of the skin, for each subject. The three measurements were then averaged for each subject. The data for skin hydration (H) is provided below.

| | Skin Hydration (H) | | |
|---|---|---|---|
| | Baseline | 2 Weeks | 4 Weeks |
| Mean | 70.8 | 51.6 | 49.5 |
| Mean Percent Difference from Baseline | | −26% | −29% |
| σ | | 14% | 12% |

The regimen showed a statistically significant decrease in Skin Hydration, H, of twenty-six percent (26%) after using the treatment regimen for two (2) weeks and a statistically significant decrease of twenty-nine (29%) after using the treatment regimen four (4) weeks compared to baseline (p=2.27 E-05 and p=5.38 E-06, respectively). A loss in skin hydration is typically observed following treatment with anti-acne products.

Example 13

Skin Cleanser of Invention with Antifungal and Antibacterial Agents

A pharmaceutical composition according to the invention may be prepared for cleansing skin as set forth below:

|  | Ingredient | Trade Name/Supplier | % by Weight |
|---|---|---|---|
| Part A | Deionized Water | N/A | 50 |
|  | Trisodium Ethylene-Diamine-Tetraacetic Acid (EDTA) | HAMP-ENE Na$_3$T/Akzo Nobel | 0.2 |
|  | Sodium Laureth-13 Carboxylate | SURFINE WLL/Finetex | 10 |
|  | Disodium Laureth Sulfosuccinate | MACKANATE EL/McIntyre Group | 17 |
|  | Disodium Cocoamphodiacetate | MONATERIC CDX-38/Mona | 11 |
|  | PEG-150 Pentaerythrityl Tetrastearate | CROTHIX/Croda | 1.5 |
|  | PEG-150 Distearate | KESSCO PEG 6000 DS/Stepan | 0.7 |
|  | Methylparaben | N/A | 0.2 |
| Part B | Clotrimazole | N/A | 0.8 |
|  | Citric Acid | N/A | 1.5 |
|  | Triclosan | IRGASAN DP300/Ciba | 0.3 |
| Part C | PPG-26-Buteth-26, PEG-40 Hydrogenated Castor Oil | SOLUBILISANT LR1/Les Colorant Wackherr SA | 2 |
|  | Fragrance (Parfum) | Fragrance - BELL #J7393/Bell Flavors and Fragrances | 0.3 |
|  | Menthol | Menthol Crystals, USP | 0.1 |
| Part D | Butylene Glycol, Deionized water, Black Cohosh (*Cimicifuga Racemosa*) Extract | ACTIPHYTE OF BLACK SNAKEROOT BG50/Active Organics | 0.1 |
|  | Butylene Glycol, Deionized water, *Camellia Oleifera* Extract | ACTIPHYTE OF JAPANESE GREEN TEA BG50/Active Organics | 0.1 |
|  | Sodium Peroxylinecarbolic Acid (PCA) | AJIDEW-50/Ajinomoto | 0.2 |
|  | Cocamidopropyl PG-Dimonium Chloride Phosphate | PHOSPHOLIPID PTC/Mona | 1 |
| Part E | Hydrogen Peroxide | Hydrogen Peroxide, 35% solution, technical | 3 |
|  |  |  | 100% |

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 6 and a viscosity between 3,000 to 4,000 cps (RVT: #4@10 rpm@25° C.).

Example 14

Skin Cleanser of Invention with Antifungal and Antibacterial Agents

A pharmaceutical composition according to the invention may be prepared for cleansing skin as set forth below:

|  | Ingredient | Trade Name/Supplier | % by Weight |
|---|---|---|---|
| Part A | Deionized Water | N/A | 50 |
|  | Trisodium Ethylene-Diamine-Tetraacetic Acid (EDTA) | HAMP-ENE Na$_3$T/Akzo Nobel | 0.2 |
|  | Sodium Laureth-13 Carboxylate | SURFINE WLL/Finetex | 10 |
|  | Disodium Laureth Sulfosuccinate | MACKANATE EL/McIntyre Group | 17 |
|  | Disodium Cocoamphodiacetate | MONATERIC CDX-38/Mona | 11 |
|  | PEG-150 Pentaerythrityl Tetrastearate | CROTHIX/Croda | 1.5 |

-continued

|  | Ingredient | Trade Name/Supplier | % by Weight |
|---|---|---|---|
|  | PEG-150 Distearate | KESSCO PEG 6000 DS/Stepan | .7 |
|  | Methylparaben | N/A | 0.2 |
| Part B | Ciclopirox Olamine | N/A | 0.8 |
|  | Citric Acid | N/A | 1.5 |
|  | Triclosan | IRGASAN DP300/Ciba | 0.3 |
| Part C | PPG-26-Buteth-26, PEG-40 Hydrogenated Castor Oil | SOLUBILISANT LR1/Les Colorant Wackherr SA | 2 |
|  | Fragrance (Parfum) | Fragrance - BELL #J7393/Bell Flavors and Fragrances | 0.3 |
|  | Menthol | Menthol Crystals, USP | 0.1 |
| Part D | Butylene Glycol, Deionized water, Black Cohosh (*Cimicifuga Racemosa*) Extract | ACTIPHYTE OF BLACK SNAKEROOT BG50/Active Organics | 0.1 |
|  | Butylene Glycol, Deionized water, *Camellia Oleifera* Extract | ACTIPHYTE OF JAPANESE GREEN TEA BG50/Active Organics | 0.1 |
|  | Sodium Peroxylinecarbolic Acid (PCA) | AJIDEW-50/Ajinomoto | 0.2 |
|  | Cocamidopropyl PG-Dimonium Chloride Phosphate | PHOSPHOLIPID PTC/Mona | 1 |
| Part E | Hydrogen Peroxide | Hydrogen Peroxide, 35% solution, technical | 3 |
|  |  |  | 100% |

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 6 and a viscosity between 3,000 to 4,000 cps (RVT: #4@10 rpm@25° C.).

Various modifications of the invention in addition to those shown and described herein will be apparent to those skilled in the art from the foregoing description. Such modifications are also intended to fall within the scope of the appended claims. The foregoing disclosure includes all the information deemed essential to enable those skilled in the art to practice the claimed invention.

What is claimed is:

1. A topical anti-inflammatory composition comprising synergistically effective combination comprising:

hydrogen peroxide in an amount sufficient to cleanse the skin;

an exfoliant selected from the group consisting of an enzymatic exfoliant and an mono- or poly-hydroxy acid;

a hydrophilic moisturizing agent in an amount sufficient to facilitate hydration of the skin;

a hydrophobic moisturizing agent in an amount sufficient to inhibit moisture loss by the skin;

an anti-inflammatory agent in an amount sufficient to reduce inflammation of the skin; and a carrier wherein the carrier comprising an amount of amphoteric surfactant and citric acid is sufficient to inhibit hydrogen peroxide decomposition for at least three months.

2. The pharmaceutical composition of claim 1, wherein the hydrogen peroxide is present in an amount from about 0.01 to 6 weight percent by weight of the composition, the moisturizing agent is present in an amount of about 0.01 to 20 weight percent by weight of the composition, and the anti-inflammatory agent is present in an amount of about 0.02 to 2 weight percent by weight of the composition.

3. The pharmaceutical composition of claim 1, wherein the hydrophobic moisturizing agent is ceramide, borage oil, tocopherol, tocopherol linoleate, dimethicone, glycerine, or a mixture thereof.

4. The pharmaceutical composition of claim 1, wherein the hydrophilic moisturizing agent is hyaluronic acid, sodium peroxylinecarbolic acid, wheat protein, hair keratin amino acids, or a mixture thereof.

5. The pharmaceutical composition of claim 1, wherein the composition further comprises a pharmaceutically acceptable carrier or excipient.

6. A gel, paste, cream, lotion, emulsion, or ointment comprising the pharmaceutical composition of claim 1.

7. The pharmaceutical composition of claim 1, wherein the exfoliant is an enzymatic exfoliant.

8. The pharmaceutical composition of claim 1, wherein the exfoliant is an mono- or -poly-hydroxy acid.

9. The pharmaceutical composition of claim 8, wherein the exfoliant comprises an alpha-hydroxy acid, beta-hydroxy acid, or tannic acid.

10. The pharmaceutical composition of claim 8, wherein the exfoliant comprises glycolic acid, lactic acid, citric acid, salicylic acid, or tannic acid.

11. The pharmaceutical composition of claim 1, wherein the amount of amphoteric surfactant and citric acid is sufficient to inhibit hydrogen peroxide decomposition at 40° C. for at least three months.

12. The pharmaceutical composition of claim 1, further comprising at least one of a surfactant, a stabilizer, a preservative, an anti-oxidant, or a coloring agent, which together may be present in an amount from about 10.1 to 99.1 weight percent of the composition.

* * * * *

UNITED STATES PATENT AND TRADEMARK OFFICE
CERTIFICATE OF CORRECTION

PATENT NO. : 6,673,374 B2
DATED : January 6, 2004
INVENTOR(S) : Howard Murad

It is certified that error appears in the above-identified patent and that said Letters Patent is hereby corrected as shown below:

<u>Column 31,</u>
Line 50, insert the word -- a -- before the word "synergistically".
Line 54, change "an" to -- a --.
Line 62, change the word "comprising" to -- comprises --.
Line 63, delete the word "is".

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,673,374 B2
APPLICATION NO. : 09/953431
DATED : January 6, 2004
INVENTOR(S) : H. Murad It is certified that error appears in the above-identified patent and that said Letters Patent is hereby corrected as shown below:

In the section titled Item (63) "Related U.S. Application Data" On Title Page, at line 2, replace "Pat. No. 6,576,948" with --Pat. No. 6,383,523--.

Signed and Sealed this

Twentieth Day of February, 2007

JON W. DUDAS
*Director of the United States Patent and Trademark Office*